United States Patent
McAlister

(10) Patent No.: US 9,540,578 B2
(45) Date of Patent: *Jan. 10, 2017

(54) ENGINEERED FUEL STORAGE, RESPECIATION AND TRANSPORT

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 23 days.

This patent is subject to a terminal disclaimer.

(21) Appl. No.: 14/273,491

(22) Filed: May 8, 2014

(65) Prior Publication Data

US 2015/0073062 A1 Mar. 12, 2015

Related U.S. Application Data

(60) Continuation of application No. 13/710,249, filed on Dec. 10, 2012, now Pat. No. 8,814,962, which is a
(Continued)

(51) Int. Cl.
*C10J 3/00* (2006.01)
*C10L 1/00* (2006.01)
(Continued)

(52) U.S. Cl.
CPC ........ *C10J 3/723* (2013.01); *B01J 7/00* (2013.01); *B01J 19/24* (2013.01); *C01B 3/001* (2013.01);
(Continued)

(58) Field of Classification Search
CPC .............. C12P 3/00; B01J 19/24; C10B 53/02
(Continued)

(56) References Cited

U.S. PATENT DOCUMENTS 3,890,113 A 6/1975 Child et al.
3,950,369 A 4/1976 Gent
(Continued)

FOREIGN PATENT DOCUMENTS

CN 1918068 A 2/2007
CN 101195775 6/2008
(Continued)

OTHER PUBLICATIONS

Deluga et al.. "AviationBioguels: Hydrotreated Renewable Jet," *General Electric*. Presentation Dated: Feb. 23, 2010. 13 pages.
(Continued)

*Primary Examiner* — Matthew Merkling
(74) *Attorney, Agent, or Firm* — Perkins Coie LLP

(57) ABSTRACT

Techniques, systems and material are disclosed for thermochemical regeneration of biomass into renewable engineered fuel, storage of the renewable engineered fuel, respeciation of the renewable engineered fuel and transport. In one aspect, a method includes generating low density hydrogen fuel from biomass dissociation at a first location of a low elevation. The low density hydrogen fuel is self-transported in a pipeline to a second location at a higher elevation than the first location by traveling from the first location to the second location without adding energy of pressure. A high density hydrogen carrier is generated at the second location of higher elevation by reacting the low density hydrogen fuel with at least one of a carbon donor, a nitrogen donor and an oxygen donor harvested from industrial waste. The high density hydrogen carrier is delivered to a third location of a lower elevation than the second location while providing pressure or kinetic energy.

20 Claims, 10 Drawing Sheets

Related U.S. Application Data division of application No. 13/027,185, filed on Feb. 14, 2011, now Pat. No. 8,328,888.

(60) Provisional application No. 61/304,403, filed on Feb. 13, 2010, provisional application No. 61/421,189, filed on Dec. 8, 2010.

(51) Int. Cl.

| | |
|---|---|
| *C12P 3/00* | (2006.01) |
| *B01J 19/24* | (2006.01) |
| *C10B 53/02* | (2006.01) |
| *F17D 1/02* | (2006.01) |
| *C10J 3/72* | (2006.01) |
| *C10G 2/00* | (2006.01) |
| *C10G 3/00* | (2006.01) |
| *B01J 7/00* | (2006.01) |
| *C01B 3/00* | (2006.01) |
| *C07C 1/04* | (2006.01) |
| *C10L 3/10* | (2006.01) |

(52) U.S. Cl.
CPC .............. *C01B 3/0015* (2013.01); *C07C 1/04* (2013.01); *C10B 53/02* (2013.01); *C10G 2/30* (2013.01); *C10G 2/32* (2013.01); *C10G 2/34* (2013.01); *C10G 2/50* (2013.01); *C10G 3/40* (2013.01); *C10L 1/00* (2013.01); *C10L 3/10* (2013.01); *C12P 3/00* (2013.01); *F17D 1/02* (2013.01); *C01B 2203/0283* (2013.01); *C10G 2300/1011* (2013.01); *Y02E 50/14* (2013.01); *Y02E 50/32* (2013.01); *Y02E 60/34* (2013.01); *Y02P 20/129* (2015.11); *Y02P 20/133* (2015.11); *Y02P 30/20* (2015.11); *Y10T 137/0318* (2015.04); *Y10T 137/8593* (2015.04)

(58) Field of Classification Search
USPC ........................................................ 48/197 R
See application file for complete search history.

(56) References Cited

U.S. PATENT DOCUMENTS

| | | | |
|---|---|---|---|
| 4,367,206 A | 1/1983 | Pinto | |
| 4,424,118 A | 1/1984 | Rankel | |
| 4,861,360 A | 8/1989 | Apffel | |
| 4,906,302 A | 3/1990 | Bruya | |
| 4,968,722 A | 11/1990 | Westerterp | |
| 5,059,303 A | 10/1991 | Taylor et al. | |
| 5,383,500 A | 1/1995 | Dwars et al. | |
| 5,630,528 A | 5/1997 | Nanaji | |
| 6,180,396 B1 | 1/2001 | Ono et al. | |
| 6,360,141 B1 | 3/2002 | Jensen | |
| 6,527,980 B1 | 3/2003 | Roden et al. | |
| 6,531,630 B2 | 3/2003 | Vidalin | |
| 6,574,603 B1 | 6/2003 | Dickson et al. | |
| 6,673,742 B2 | 1/2004 | Abdo et al. | |
| 6,745,801 B1 | 6/2004 | Cohen et al. | |
| 6,781,014 B1 | 8/2004 | Vidalin et al. | |
| 6,875,794 B2 | 4/2005 | Seiki et al. | |
| 6,894,080 B2 | 5/2005 | Seiki et al. | |
| 6,984,305 B2 | 1/2006 | McAlister | |
| 7,082,969 B1 | 8/2006 | Hollerback | |
| 7,284,575 B2 | 10/2007 | Gram et al. | |
| 7,602,143 B2 | 10/2009 | Capizzo | |
| 7,608,439 B2 | 10/2009 | McTavish et al. | |
| 7,608,743 B2 | 10/2009 | Olah et al. | |
| 7,913,664 B2 | 3/2011 | Williams et al. | |
| 7,989,507 B2 | 8/2011 | Rising | |
| 8,070,835 B2 | 12/2011 | McAlister | |
| 8,215,342 B2 | 7/2012 | McLean et al. | |
| 8,328,888 B2 | 12/2012 | McAlister | |
| 8,352,071 B2 | 1/2013 | Winsness | |
| 8,354,456 B2 | 1/2013 | Yagi et al. |
| 8,485,233 B2 | 7/2013 | Allinson et al. |
| 8,617,260 B2 | 12/2013 | McAlister |
| 8,623,925 B2 | 1/2014 | McAlister |
| 8,784,661 B2 | 7/2014 | McAlister |
| 8,814,962 B2 | 8/2014 | McAlister |
| 8,840,692 B2 | 9/2014 | McAlister |
| 9,133,011 B2 | 9/2015 | McAlister |
| 9,174,185 B2 | 11/2015 | McAlister |
| 2002/0147107 A1 | 10/2002 | Abdo et al. |
| 2003/0062270 A1 | 4/2003 | McAlister |
| 2003/0135077 A1 | 7/2003 | O'Rear et al. |
| 2003/0196810 A1 | 10/2003 | Vinegar et al. |
| 2004/0204503 A1 | 10/2004 | Beyer |
| 2004/0247499 A1 | 12/2004 | Matsuoka et al. |
| 2005/0055874 A1 | 3/2005 | Bekemeyer |
| 2006/0169350 A1 | 8/2006 | Hollerback |
| 2007/0137246 A1 | 6/2007 | McKellar et al. |
| 2007/0244208 A1 | 10/2007 | Shulenberger et al. |
| 2007/0298478 A1 | 12/2007 | Offerman et al. |
| 2008/0072496 A1 | 3/2008 | Yogev et al. |
| 2008/0243310 A1 | 10/2008 | Esposito et al. |
| 2008/0264254 A1 | 10/2008 | Song et al. |
| 2009/0005903 A1 | 1/2009 | Winsness |
| 2009/0286890 A1 | 11/2009 | Joshi et al. |
| 2009/0289227 A1 | 11/2009 | Rising |
| 2009/0313886 A1 | 12/2009 | Hinman et al. |
| 2009/0318572 A1 | 12/2009 | Sakai et al. |
| 2010/0205856 A1 | 8/2010 | Kubic et al. |
| 2011/0000579 A1 | 1/2011 | Allinson et al. |
| 2011/0061376 A1 | 3/2011 | McAlister |
| 2011/0061383 A1 | 3/2011 | McAlister |
| 2011/0120589 A1 | 5/2011 | Evans |
| 2011/0203669 A1 | 8/2011 | McAlister |
| 2011/0288738 A1 | 11/2011 | Donnelly et al. |
| 2011/0291425 A1 | 12/2011 | Juranitch |
| 2012/0149786 A1 | 6/2012 | McAlister |
| 2012/0167456 A1 | 7/2012 | McAlister |
| 2012/0197460 A1 | 8/2012 | Seymour et al. |
| 2012/0205004 A1 | 8/2012 | Webb |
| 2013/0036670 A1 | 2/2013 | McAlister |
| 2013/0112313 A1 | 5/2013 | Donnelly et al. |
| 2015/0068110 A1 | 3/2015 | McAlister |

FOREIGN PATENT DOCUMENTS

| | | |
|---|---|---|
| CN | 101225318 | 7/2008 |
| CN | 101448979 A | 6/2009 |
| CN | 101568624 | 10/2009 |
| CN | 101743343 | 7/2012 |
| CN | 102844408 | 6/2015 |
| DE | 3140028 | 5/1982 |
| DE | 3933285 A1 | 4/1991 |
| EP | 1002767 A2 | 5/2000 |
| EP | 1219585 A2 | 7/2002 |
| EP | 2534362 | 12/2012 |
| EP | 2742117 | 6/2014 |
| FR | 2897066 A1 | 8/2007 |
| GB | 2086416 A | 5/1982 |
| JP | 02194090 | 7/1990 |
| JP | 762356 | 3/1995 |
| JP | 2000140621 | 5/2000 |
| JP | 2002193858 | 7/2002 |
| JP | 2003510403 A | 3/2003 |
| JP | 2004315473 | 11/2004 |
| JP | 2005075925 A | 3/2005 |
| JP | 2005511467 | 4/2005 |
| JP | 2005-289856 A | 10/2005 |
| JP | 2005289856 | 10/2005 |
| JP | 2005530892 | 10/2005 |
| JP | 2007314745 | 12/2007 |
| JP | 2008537956 A | 10/2008 |
| JP | 2009242154 | 10/2009 |
| JP | 2009242248 A | 10/2009 |
| JP | 2012511493 | 5/2012 |
| WO | WO-2004092055 A2 | 10/2004 |
| WO | WO-2005021474 A1 | 3/2005 |
| WO | WO-2005033250 A2 | 4/2005 |

(56) References Cited

FOREIGN PATENT DOCUMENTS

| WO | WO-2010078035 A2 | 7/2010 |
|---|---|---|
| WO | 2011100729 | 8/2011 |
| WO | 2013025646 | 2/2013 |

OTHER PUBLICATIONS

Dolan, Eric "Device uses sunlight to make liquid fuel". *The Raw Story*. Published: Dec. 24, 2010. 3 pages.
International Search Report and Written Opinion for Application No. PCT/US2011/024799 Applicant: McAlister Technologies, LLC.; Date of Mailing: Oct. 18, 2011 (9 pages).
Lee et al.. "Biological Hydrogen Production: Prospects and Challenges". *Trends in Biotechnology* 28.5. Jan. 2010. 10 pages.
Lopez et al., "Performance of the Southern California Edison Company Stirling Dish," Contractor Report, Prepared by Sandia National Laboratories Albuquerque, New Mexico, California, Printed Oct. 1993, 213 pages.
International Search Report and Written Opinion for Application No. PCT/US2012/050670 Applicant: McAlister Technologies, LLC; Date of Mailing Feb. 26, 2013 (14 pages).
European Search Report for Application No. EP11742986.0 Applicant McAlister Technologies, LLC.; Date Mailed Feb. 17, 2014. 7 pages.
European Search Report for Application No. EP11742995.1; Applicant: McAlister Technologies, LLC; Date of Mailing: Feb. 20, 2014; 7 pages.
European Search Report for Application No. EP11861833.9; Applicant: McAlister Technologies, LLC; Date of Mailing: May 2, 2014; 6 pages.
European Search Report for Application No. EP12823888.8; Applicant: McAlister Technologies, LLC; Date of Mailing: May 26, 2015; 9 pages.
International Search Report and Written Opinion for Application No. PCT/US2011/064034; Applicant: McAlister Technologies, LLC; Date of Mailing: Jan. 28, 2013; 9 pages.
International Search Report and Written Opinion for Application No. PCT/US2012/050656; Applicant: McAlister Technologies, LLC; Date of Mailing Feb. 26, 2013; 10 pages.
International Search Report and Written Opinion for Application No. PCT/US2014/029593; Applicant: McAlister Technologies, LLC; Date of Mailing: Jul. 24, 2014; 12 pages.
Notice of Rejection for Japanese Application No. 2013-543361; Applicant: McAlister Technologies, LLC; Date of Mailing: Sep. 30, 2014; 5 pages.
Sinnott, R.K., "Chemical Engineering Design," 4th ed., Butterworth-Heinemann, 2005, p. 402.

ENGINEERED FUEL STORAGE, RESPECIATION AND TRANSPORT

CLAIM OF PRIORITY

The present application is a continuation of U.S. patent application Ser. No. 13/710,249 filed on Dec. 10, 2012, which is a division of U.S. patent application Ser. No. 13/027,185 filed on Feb. 14, 2011, now U.S. Pat. No. 8,328,888, which claims the benefit of the earlier filing date of U.S. Patent Application No. 61/304,403, filed on Feb. 13, 2010 and claims the benefit of the earlier filing date of U.S. Patent Application No. 61/421,189, filed on Dec. 8, 2010. Each of these applications is incorporated herein by reference in its entirety. To the extent the foregoing application and/or any other materials incorporated herein by reference conflict with the disclosure presented herein, the disclosure herein controls.

BACKGROUND

This application relates to devices, techniques and materials related to biofuels.

Engineered fuel such as pure hydrogen and methane gases are difficult and costly to store and transport. For example, compressors needed to pressurize hydrogen and/or methane and other products can involve sizeable capital expenditures, large expenditures for electricity and attendant production of greenhouse gases, and high operating costs. Further, the pipelines for transporting the pressurized hydrogen and/or methane often incur costly maintenance and repair costs.

In addition to the compressed-gas fuel form, hydrogen can be converted to cryogenic liquid or slush for storage. Liquid hydrogen is generally stored at −420° F. (−252° C.) at atmospheric pressure and often transported through unprotected delivery lines, parts of which can be damaged due to atmospheric water vapor condensation and freezing. Storage and transport of cryogenic methane face similar costs.

Moreover, the high cost of storage and transport for hydrogen and methane is met with low energy density. For example, a gallon of cryogenic liquid methane at −256° C. provides an energy density of 89,000 BTU/gal about 28% less than a gallon of gasoline. Liquid hydrogen at −252° C. provides only about 29,700 BTU/gal or 76% less than gasoline.

SUMMARY

Techniques, structures, apparatus and materials are disclosed for thermochemical regeneration of biomass into renewable engineered fuel, storage of the generated renewable engineered fuel, respeciation of the renewable engineered fuel and transport.

In one aspect, a method of transporting renewable fuel can include generating low density hydrogen fuel from biomass dissociation at a first location of a low elevation. The low density hydrogen fuel can be self-transported in a pipeline to a second location at a higher elevation than the first location. The low density hydrogen fuel travels from the first location to the second location without adding energy or pressure. A high density hydrogen carrier is generated at the second location of higher elevation by reacting the low density hydrogen fuel with at least one of a carbon donor, a nitrogen donor and an oxygen donor. The high density hydrogen carrier is delivered to a third location of a lower elevation than the second location while providing pressure or kinetic energy.

Implementations can optionally include one or more of the following features. Generating the low density hydrogen fuel can include applying waste heat recovered from an external energy source or heat generated from a renewable energy source. The high density hydrogen carrier can include at least one of hydrocarbon, alcohol and ammonia. The hydrocarbon can include at least one of methane and ethane. The alcohol can include at least one of methanol and ethanol. The carbon donor can include carbon dioxide and the hydrogen donor can include water. The method can include dissolving a hazardous contaminant in the high density hydrogen carrier to generate a liquid mixture that isolates the hazardous contaminant from an environment. The liquid mixture can control a vapor pressure or availability of the vapor pressure. The method can include applying heat to the liquid mixture to generate oxygenated fuel mixture with a ratio of hydrogen to carbon that is higher than the high density hydrogen carrier. The method can include transporting in a pipeline the hydrogen generated from the liquid mixture to a fourth location at a higher elevation than the third location without adding energy or pressure. The method can include applying heat to the high density hydrogen carrier to generate oxygenated fuel with a ratio of hydrogen to carbon that is higher than the high density hydrogen carrier. The method can include transporting in a pipeline the hydrogen generated from the high density hydrogen carrier to a fourth location at a higher elevation than the third location without adding energy or pressure. The at least one of a carbon donor, a nitrogen donor and an oxygen donor can be harvested from industrial waste.

In another aspect, a pipeline system of transporting renewable fuel can include a biomass conversion plant at a first location of a low elevation to generate low density hydrogen fuel from biomass dissociation. A first pipeline connects the biomass conversion plant to a second location of a higher elevation than the first location. The low density hydrogen fuel travels within the pipeline from the first location to the second location without added energy of pressure. A thermochemical reactor is connected to the second location of the higher elevation to generate a high density hydrogen carrier. The thermochemical reactor reacts the low density hydrogen fuel with at least one of a carbon donor, a nitrogen donor and an oxygen donor. A second pipeline connects the thermochemical reactor to a third location of a lower elevation than the second location. The high density hydrogen carrier is delivered to the third location with at least one of pressure or kinetic energy generated by the high density hydrogen carrier.

Implementations can optionally include one or more of the following features. The thermochemical reactor can include a countercurrent heat exchanger to apply waste heat recovered from an external energy source or heat generated from a renewable energy source. The high density hydrogen carrier can include at least one of hydrocarbon, alcohol and ammonia. The hydrocarbon can include at least one of methane and ethane. The alcohol can include at least one of methanol and ethanol. The carbon donor can include carbon dioxide and the hydrogen donor can include water. The pipeline system can include a contaminant recovery system connected to the thermochemical reactor. The contaminant recovery system can be configured to harvest a hazardous contaminant; and dissolve the harvested hazardous contaminant in the high density hydrogen carrier to generate a liquid mixture that isolates the hazardous contaminant from an environment. The liquid mixture can control a vapor pressure or availability of the vapor pressure. The liquid mixture can be transported in the second pipeline to the third location using at least one of pressure and kinetic energy generated by the liquid mixture. The pipeline system can include a second thermochemical reactor connected to the third location to dissociate the liquid mixture, using an anaerobic reaction, to generate an oxygenated fuel mixture with a ratio of hydrogen to carbon that is higher than the high density hydrogen carrier. The pipeline system can include a second countercurrent heat exchanger connected to the second thermochemical reactor to apply heat to the liquid mixture to generate the oxygenated fuel mixture. The pipeline system can include a third pipeline connecting the second thermochemical reactor at a fourth location of a higher elevation than the third location without adding energy or pressure. The at least one of carbon donor, nitrogen donor and the oxygen donor can be harvested from an industrial process.

The subject matter described in this specification potentially can provide one or more of the following advantages. For example, the described techniques and systems can be used to avoid the high costs of compressing or cryogenically freezing biofuels, such as hydrogen and methane fuels. In addition, the costs associated with maintaining a pipeline for transporting gaseous and liquefied hydrogen fuel can be avoided. The described techniques can be used to selectively respeciate a given renewable fuel for efficient storage and transport.

BRIEF DESCRIPTION OF THE DRAWINGS

Like reference symbols and designations in the various drawings indicate like elements.

DETAILED DESCRIPTION

Techniques, structures, apparatus and materials are disclosed for thermochemical regeneration of biomass waste into renewable engineered fuel, storage of the generated renewable engineered fuel, respeciation of the renewable engineered fuel and transport of the engineered fuel. The economic barrier to hydrogen transportation and storage is high due to the low-dense nature of hydrogen. The described techniques and systems take advantage of that low-dense nature. As described herein, the low density hydrogen is generated from biomass waste at the source of biomass waste at a low elevation location and self-delivered to a higher elevation second location. Hydrogen is respeciated to a dense hydrogen carrier (hydrocarbon, alcohol) which is delivered to a lower elevation third location as a part of a energy divergence process. The delivery to the lower elevation provides either pressure or kinetic energy at the low elevation.

Figure 1:
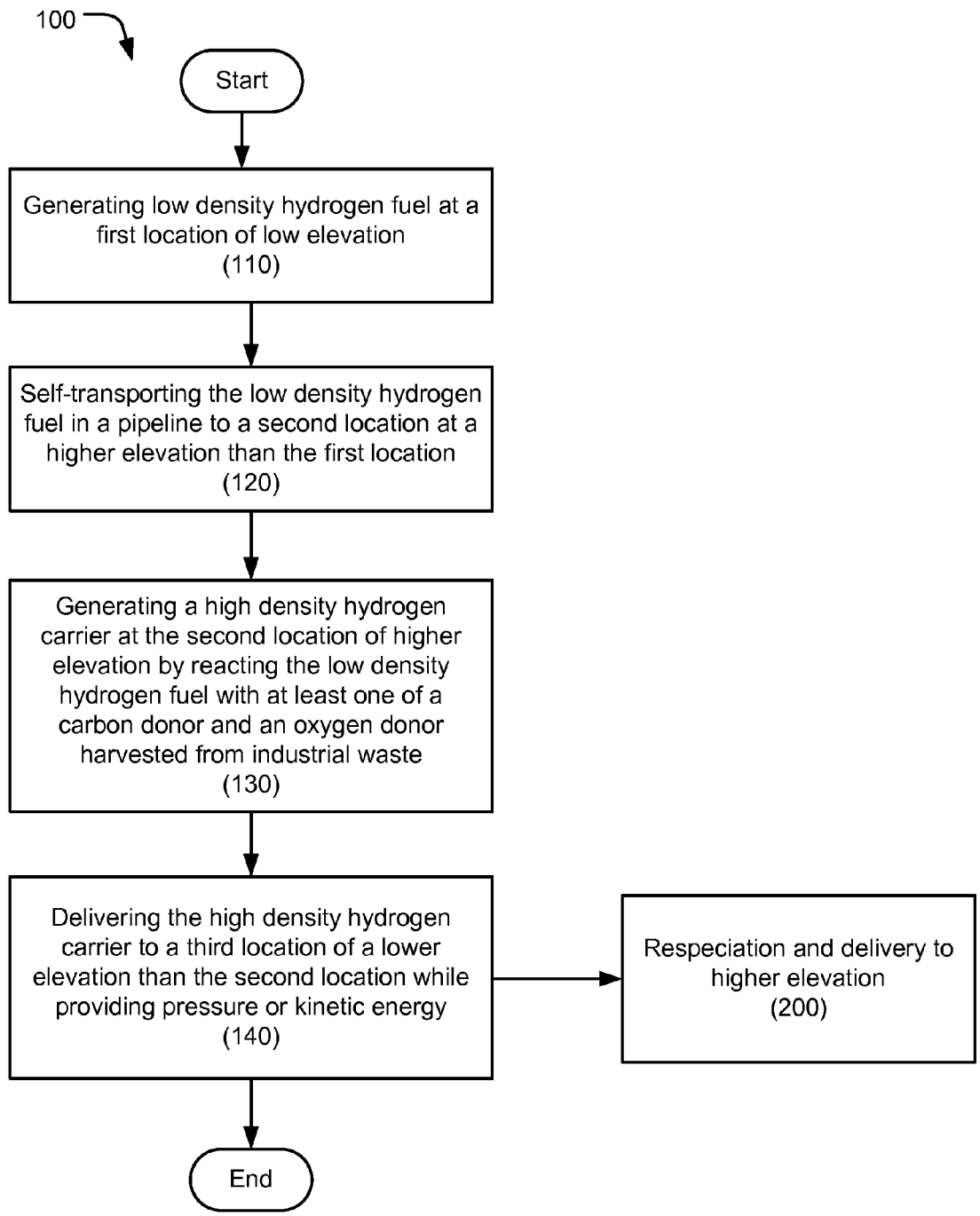
FIG. 1 is a process flow diagram of an exemplary process for generating renewable fuel from biomass waste at one location, selectively respeciating the generated renewable fuel for storage and/or transport to another location.

FIG. 1 is a process flow diagram of an exemplary process 100 for generating renewable fuel from biomass waste at one location, selectively respeciating the generated renewable fuel for storage and/or transport to another location. A system (e.g., system 400) generates low density hydrogen fuel (e.g., hydrogen gas) from biomass dissociation at a first location of a low elevation (110). The process of biomass dissociation to generate the low density hydrogen is described in a copending U.S. Patent Application entitled "Carbon-Based Durable Goods and Renewable Fuel from Biomass Dissociation," U.S. Patent Application No. 13/027, 068 filed Feb. 14, 2011, now U.S. Pat. No. 8,318,997, the entire contents of which are incorporated by reference. Also, the biomass dissociation to generate hydrogen is further described with respect to FIGS. 5 and 6.

The generated hydrogen is self-transported from the low elevation location to a second location of a higher elevation (120). Because the density of the generated hydrogen is low, the hydrogen gas freely rises to the higher elevation second location without any added energy or pressure. At the higher elevation second location, the freely transported hydrogen fuel is converted to a denser species of hydrogen carriers, such as hydrocarbon, alcohol, etc. (130). For example, at the second location of higher elevation, the low density hydrogen can be reacted with at least one of a carbon donor (e.g., $CO_2$) and an oxygen donor (e.g., $H_2O$) harvested from industrial waste to generate hydrocarbons, alcohols, ammonia, etc.

The generated high density hydrogen fuel can be transported to a third location of a lower elevation (140). For example, liquid methanol can produce a 'head' in a pipeline on delivery to the lower elevation third location as the liquid methanol descends and gains kinetic energy. The delivered methanol can provide energy conversion by turning a turbine, for example as methanol descends to the third location.

Figure 2:
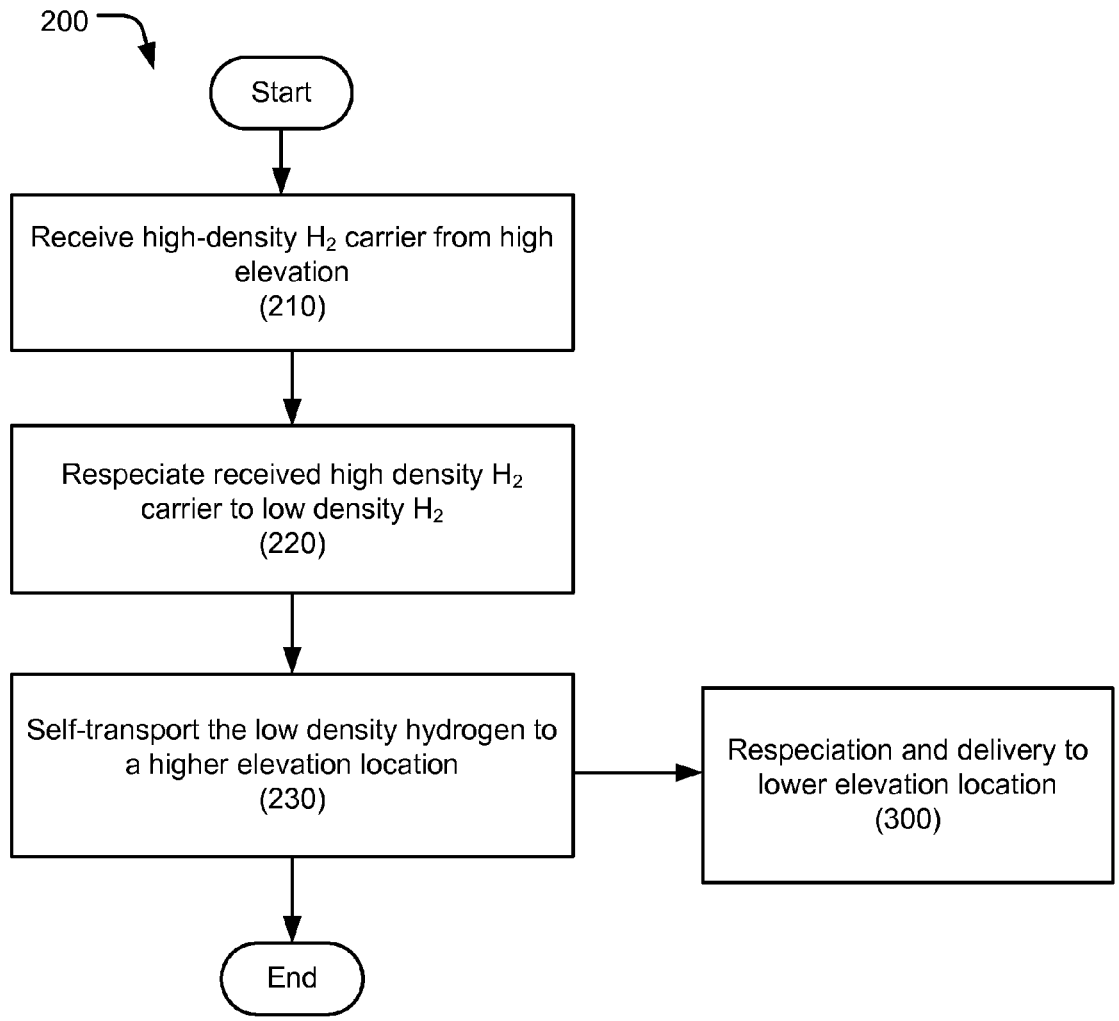
FIG. 2 is a process flow diagram of an exemplary process for respeciating high density hydrogen carrier fuel at a lower elevation to a low density hydrogen fuel and delivering the respeciated fuel to a higher elevation.

The renewable fuel deliver can continue by respeciating the high-density hydrogen fuel at the third location of low elevation to a low density hydrogen fuel and self-transporting the respeciated hydrogen fuel to a fourth location of a higher elevation. FIG. 2 is a process flow diagram of an exemplary process 200 for respeciating high density hydrogen carrier fuel at a lower elevation to a low density hydrogen fuel and delivering the respeciated fuel to a higher elevation. A system (e.g., system 400) receives the higher density hydrogen carrier from the higher elevation location (210). The system respeciates the received higher density hydrogen carrier to obtain low density hydrogen fuel (220). The low density hydrogen fuel is self-transported to a higher elevation location (230). The self-transported hydrogen fuel can be respeciated and delivered to a lower elevation location again as shown in the process 300 of FIG. 3 below.

Figure 3:
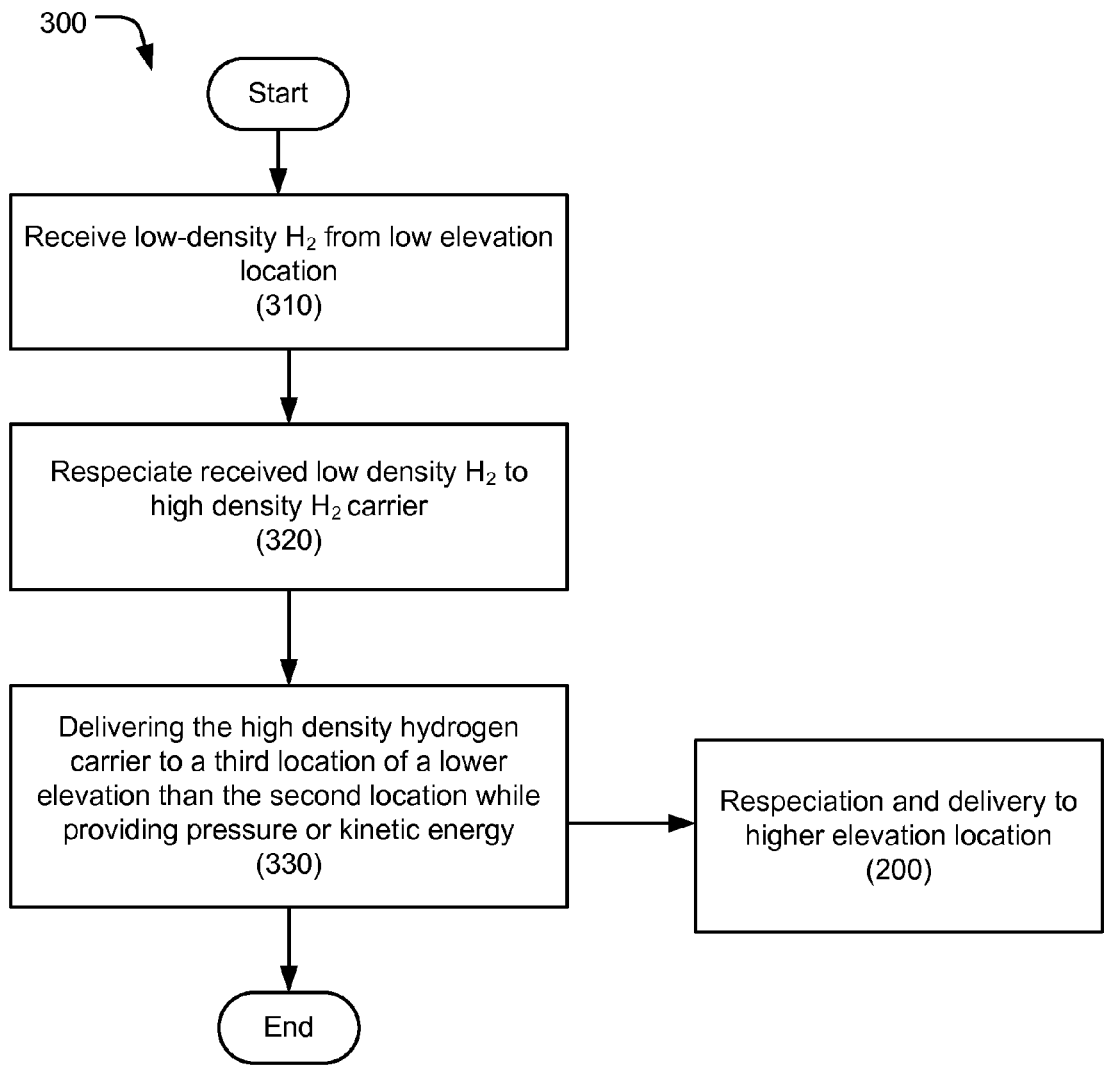
FIG. 3 is a process flow diagram of an exemplary process for respeciating the low density hydrogen fuel at the high elevation location to obtain a high density hydrogen carrier fuel and deliver the respeciated fuel to a lower elevation location.

To continue transporting the renewable fuel, the low density hydrogen fuel received at the higher elevation location is respeciated and delivered to a lower elevation location. FIG. 3 is a process flow diagram of an exemplary process 300 for respeciating the low density hydrogen fuel at the high elevation location to obtain a high density hydrogen carrier fuel and deliver the respeciated fuel to a lower elevation location. A system (e.g., system 400) receives the low density hydrogen fuel from the lower elevation location (310). The system respeciates the received low density hydrogen fuel to obtain high density hydrogen carrier fuel (320). The high density hydrogen carrier fuel is self-transported to a higher elevation location (330).

The selective respeciation and delivery of the renewable fuel as shown and described in processes 200 and 300 are alternately performed until the renewable fuel is delivered to a desired location. Describe below are processes and systems for respeciating and delivering various species of the renewable fuel.

Figure 4:
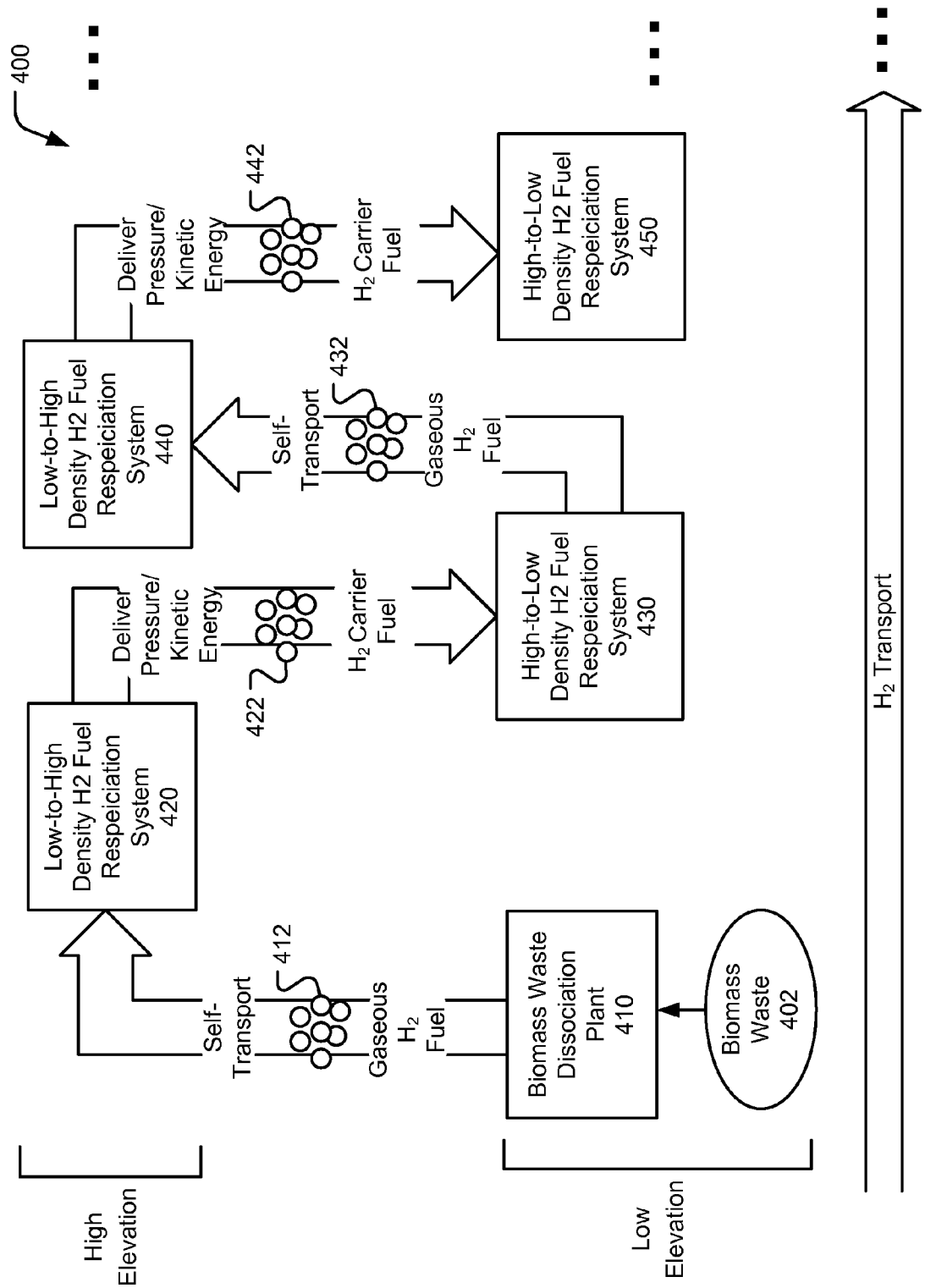
FIG. 4 is a block diagram of a system for generating renewable fuel from biomass waste, selectively respeciating the generated fuel and delivering the selectively respeciated fuel to a target location.

FIG. 4 is a block diagram of a system 400 for generating renewable fuel from biomass waste 402, selectively respeciating the generated fuel and delivering the selectively respeciated fuel to a target location. The system 400 includes a biomass dissociation plant 410 at the source of the biomass waste 402, such as a burnt down forest. The biomass waste dissociation plant performs biomass dissociation to generate various species of hydrogen fuel including low density hydrogen 412 as described in the copending U.S. Patent Application entitled "Carbon-Based Durable Goods and Renewable Fuel from Biomass Dissociation," U.S. Patent Application No. 13/027, 068, filed Feb. 14, 2011, now U.S. Pat. No 8,318,997, the entire contents of which are incorporated by reference. Also, the biomass dissociation to generate various species of hydrogen is further described with respect to FIGS. 5 and 6 below.

The low density hydrogen fuel (e.g., gaseous hydrogen) 412 is self-transported to a low-to-high density hydrogen fuel respeciation system 420 at a higher elevation location. The specific reactions for respeciating the low density hydrogen fuel to obtain high density hydrogen carrier 422 is described further below.

The high density hydrogen carrier fuel (e.g., gaseous hydrogen) 422 is delivered to a high-to-low density hydrogen fuel respeciation system 430 at a lower elevation location. The specific reactions for respeciating the high density hydrogen carrier fuel to obtain low density hydrogen fuel is described further below.

The system can include additional numbers of low-to-high density hydrogen fuel respeciation systems and high-to-low density hydrogen fuel respeciation systems as needed to deliver the renewable fuel to a desired target location. For example, the system 400 in FIG. 4 is shown in include a second low-to-high density hydrogen fuel respeciation system 440 and a second high-to-low density hydrogen fuel respeciation system 450 for illustrative purposes only.

For the example shown in FIG. 4, the high-to-low density hydrogen fuel respeciation system 430 respeciates the high density hydrogen carrier fuel to obtain low density hydrogen fuel 432, which is self-transported to the second low-to-high density hydrogen fuel respeciation system 440 at the higher elevation. The second low-to-high density hydrogen fuel respeciation system 440 respeciates the low density hydrogen fuel to obtain high density hydrogen carrier fuel 442, which is delivered to the second high-to-low density hydrogen fuel respeciation system 450.

The system 400 can be implemented at a coastal area where there are several peaks and valleys. Also, the system 400 can be implemented in metropolitan locations where there are several tall buildings. For examples, hydrogen can be produced at the base of one building and deliver to the top of the building. Energy conversion can be performed at the top of the building to respeciate the fuel to generate water and deliver the generated water to the bottom of the building. Also, at the top of the building, the hydrogen fuel can be converted to hydrocarbon, alcohol or ammonia and have it delivered to a bottom of another building as an energy conversion step. The respeciation and transport processes can continues from one building to another or from a valley to a peak and from the peak to another valley until the fuel is delivered to a target location.

The overall energy for the transportation process can be favorable due to the self-transportable nature of the low density hydrogen fuel and the self-generated pressure and/or kinetic energy of the high density hydrogen carrier fuel. Also, the carbon and/or hydrogen donors used in the respeciation processes can be harvested and recycled from industrial processes (e.g., $CO_2$ from fossil fuel exhausts).

Biomass Waste Dissociation

Figure 5:
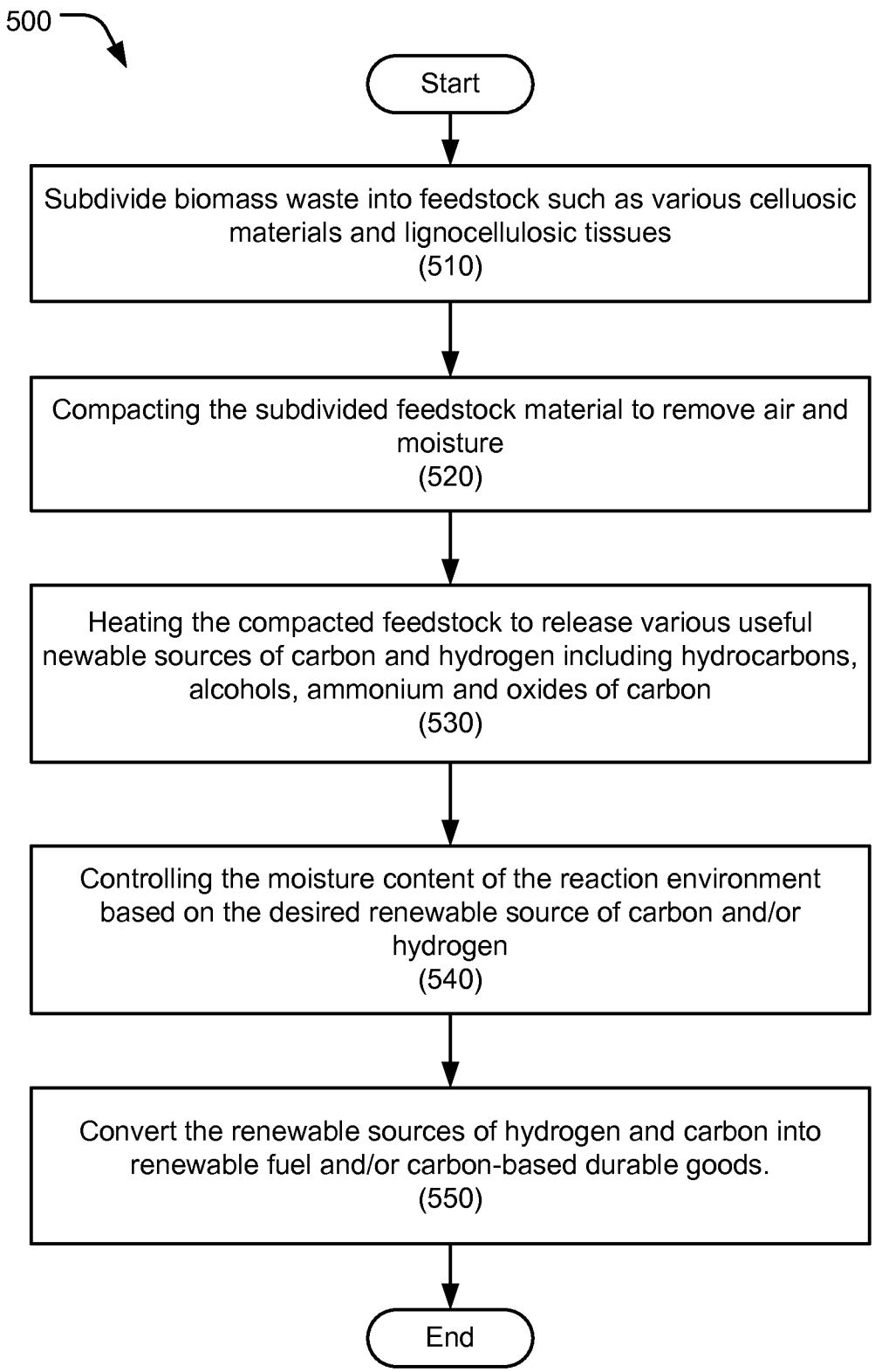
FIG. 5 shows a process flow diagram of a process for a rapid conversion of carbon, hydrogen and oxygen containing biomass wastes into useful renewable sources of carbon and hydrogen that can be used to produce carbon-based durable goods and renewable fuel.

FIG. 5 shows a process flow diagram of a process 500 for a rapid conversion of carbon, hydrogen and oxygen containing biomass wastes into useful renewable sources of carbon and hydrogen that can be used to produce carbon-based durable goods and renewable fuel. The process 500 is analogous to process 110 in FIG. 1 above.

A system (e.g., a biomass dissociation system 600 below) can subdivide the biomass waste into feedstock materials such as various cellulosic materials and lignocellulosic tissues (510). The subdivided feedstock materials can be compacted to remove air and moisture (520). The compacted biomass waste feedstock can be heated to release various useful renewable sources of carbon and/or hydrogen including hydrocarbons, alcohols, ammonium, and oxides of carbon (530). Also, the moisture content of the overall reaction environment can be controlled based on the desired renewable source of carbon and/or hydrogen (540). To control the moisture content, the compacted biomass waste feedstock that has been completely dried and de-aired can be used as a desiccant, for example. The renewable sources of hydrogen and carbon can be used to generate renewable fuel and/or carbon-based durable goods (550)

For example, as shown in Equation 1, biomass wastes can be heated sufficiently in an anaerobic environment to release desirable gases, carbon, and solid residues such as mineral oxides and other compounds. The anaerobic process for oxides of carbon and co-production of hydrogen and/or hydrocarbons from biomass wastes summarized in Equation 1 is not balanced for any particular type, amount, or ratio of lignin, cellulose, or other biomass feedstock.

$$C_xH_yO_z + HEAT \rightarrow CH_4 + H_2 + CO_2 + CO \qquad \text{Equation 1}$$

Using the process described in Equation 1, virtually any organic material can be converted in large part to hydrocarbon fuel, such as methane ($CH_4$) for distribution and storage in the existing natural gas infrastructure. Equation 2 below illustrates a general summary of the overall reactions for production of methane from typical biomass wastes such as glucose, lignin, and cellulosic feedstocks.

$$C_6H_{12}O_6 + HEAT \rightarrow 3CH_4 + 3CO_2 \quad \text{Equation 2}$$

In some implementations, the biomass dissociation reaction can produce alcohols, such as methanol as a readily storable and transportable liquid fuel and chemical precursor. Methanol or "wood alcohol" can be extracted by heating lignocellulosic wastes through partial combustion or by anaerobic heating processes. Equations 3 and 4 summarize the output of methanol that can be achieved by selection of different anaerobic operating temperatures, pressures, and catalysts.

$$C_6H_{12}O_6 + HEAT \rightarrow 6CO + 6H_2 \quad \text{Equation 3}$$

$$6CO + 6H_2 \rightarrow 3CH_3OH + 3CO \quad \text{Equation 4}$$

At higher feed rates and/or lower heat release rates in a reactor, the charge does not reach the higher temperatures that produce the gases shown in Equation 1, and thus the dissociation process produces alcohol, such as methanol. Carbon monoxide can be separated from methanol by cooling the methanol vapors to form liquid methanol and to utilize the separated carbon monoxide to fuel a combustible engine, to release heat through combustion by a burner assembly, and to form hydrogen by a reaction with water as summarized in Equation 5. Hydrogen produced by the reaction summarized in Equation 5 may be used to produce methanol as shown in Equation 4, to improve operation of an engine, to improve the yield of methane and/or ethane in the biomass conversion and/or as a heating fuel.

$$CO + H_2O \rightarrow H_2 + CO_2 \quad \text{Equation 5}$$

Figure 6:
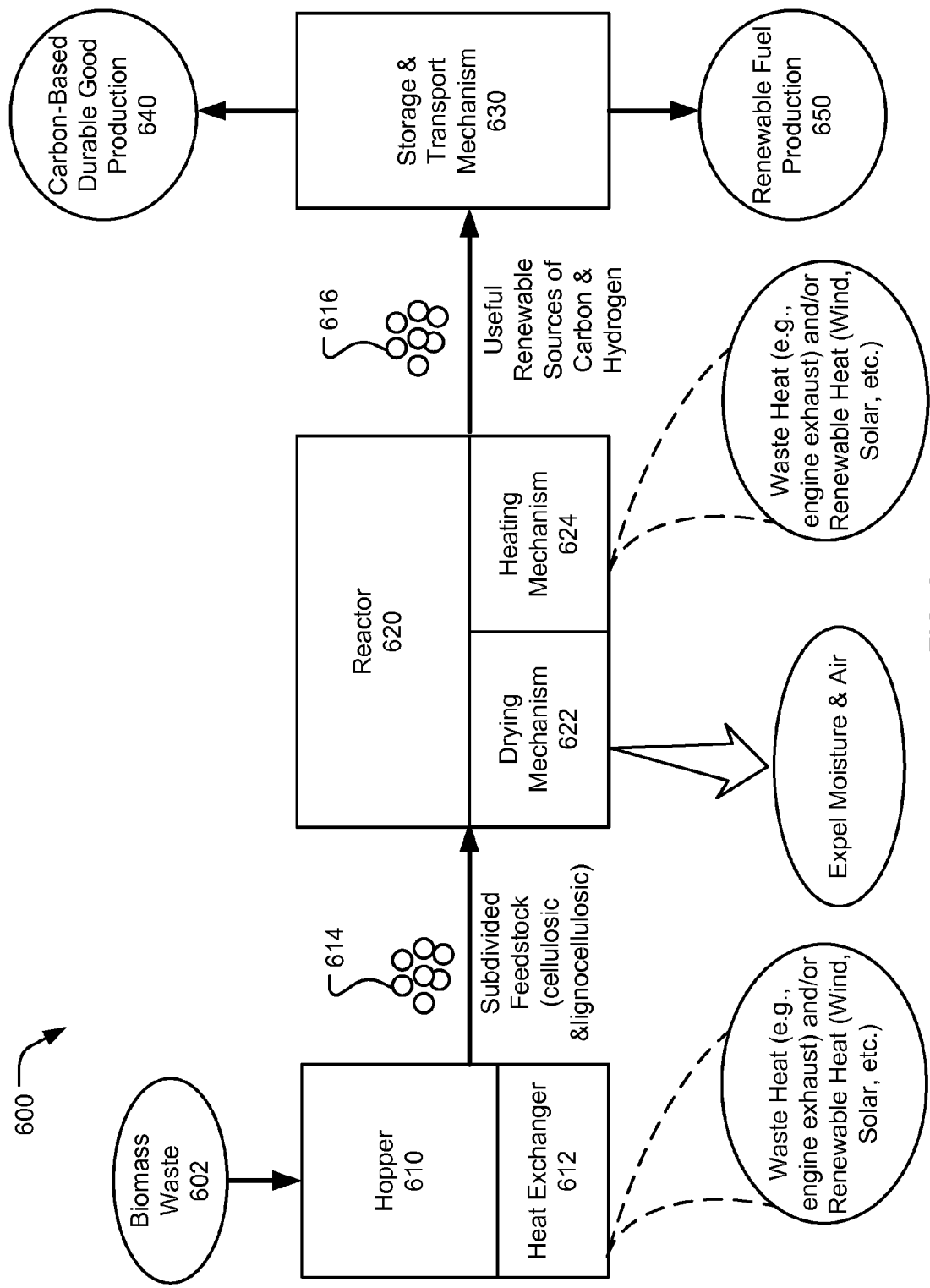
FIG. 6 shows an exemplary system for dissociating biomass waste into hydrogen and carbon carrying intermediaries.

FIG. 6 shows an exemplary system 600 for dissociating biomass waste 602 into hydrogen and carbon carrying intermediaries. The system 600 is analogous to the system 410 in FIG. 4 above. The system 600 includes a biomass waste intake component, such as a hopper 610 that receives the biomass waste in raw form and breaks down (e.g., chips, chops, grinds, etc.) the raw material into subdivided feedstock 614, such as various cellulosic and lignocellulosic materials. The hopper 610 can include a heating mechanism, such as a heat exchanger 612 to pre-heat the subdivided feedstock. The heat exchanger can recapture and recycle waste heat from an external heat source (e.g., engine exhaust and/or renewable heat, such as wind, solar, etc.) or from the reactor 620.

The subdivided (and in some implementations, pre-heated) feedstock is forwarded to a reactor 620 to dissociate the biomass waste feedstock into useful renewable sources of carbon and hydrogen, such as various hydrocarbons, alcohols, ammonia, and oxides of carbon. The reactor can include a drying mechanism 622 to expel moisture and air from the feedstock. The drying mechanism 622 can include an extruding device to physically 'squeeze out' the moisture and air from the feedstock. Examples of the extruding device include a helical screw conveyer and a ram piston conveyer. Also, the drying mechanism 622 can include one or more heating mechanisms, such as heat exchangers that capture heat generated by the reactor 620 and recycle the captured heat to dry the feedstock. The heat exchangers can also recapture and recycle waste heat from an external heat source (e.g., engine exhaust and/or renewable heat, such as wind, solar, etc.)

The reactor 620 can also include a heating mechanism 624 for generating adequate heat used in an anaerobic reaction to dissociate the biomass waste feedstock into the useful renewable sources of carbon and hydrogen 616, such as hydrocarbons, alcohols, ammonia and oxides of carbon. The generated useful renewable sources of carbon and hydrogen 616 can be forwarded to a storage and/or transport mechanism 630 to be used in additional reaction to generate renewable fuel and/or carbon-based durable goods in respective reaction systems 640 and 650. Moreover, the storage and/or transport mechanism 630 allows for efficient transport of the useful renewable sources of carbon and hydrogen 616 to remote locations for further processing.

The reactor 620 can be configured to increase thermal efficiency of the biomass waste conversion process while reducing or eliminating carbon dioxide formation. For example, the reactor 620 can include mechanisms to perform various countercurrent drying (e.g., recycling heat) and elimination of air, moisture, and other oxygen donors prior to extraction of carbon, hydrocarbons such as methane, and/or hydrogen.

Figure 7:
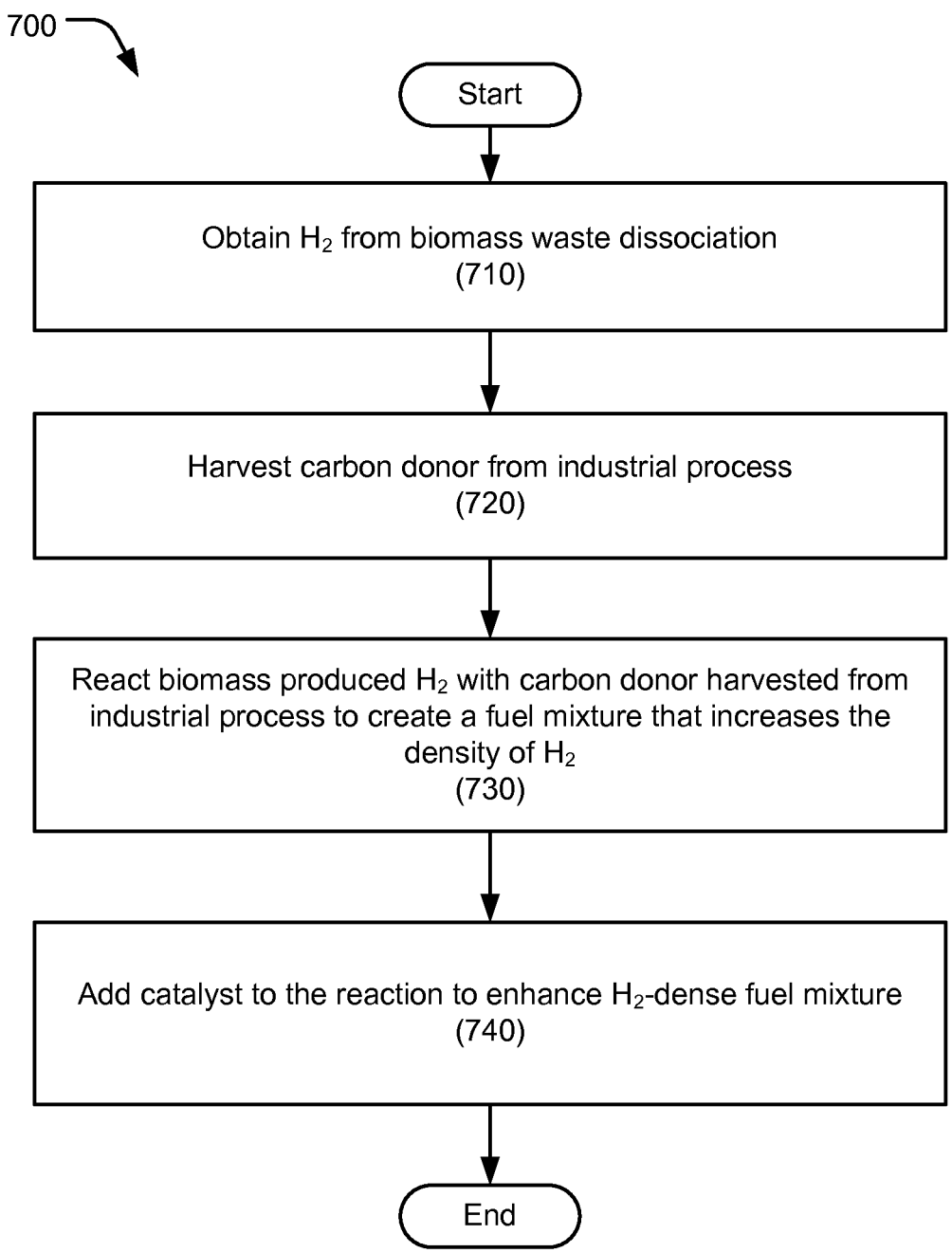
FIG. 7 is a process flow diagram of a process for generating high density hydrogen carriers by reinvesting, repurposing or recycling carbon dioxide harvested from waste generated by industrial processes to react with low density hydrogen from biomass waste dissociation.

Respeciation of Low Density hydrogen Fuel to Generate High Density hydrogen Carrier The low density hydrogen fuel can be respeciated to generate high density hydrogen Carrier, such as hydrocarbons, alcohols and ammonia as described in the copending U.S. Patent Application entitled "CARBON RECYCLING AND REINVESTMENT USING THERMOCHEMICAL REGENERATION," U.S. Patent Application No. 13/027,196 filed Feb. 14, 2011, now U.S. Pat. No. 8,912,239, the entire contents of which is incorporated by reference. For example, FIG. 7 is a process flow diagram of a process 700 for generating high density hydrogen carriers by reinvesting, repurposing or recycling carbon dioxide harvested from waste generated by industrial processes to react with low density hydrogen from biomass waste dissociation. A system (e.g., system 800 below) harvests a carbon donor from industrial processes (710). The carbon donor, such as carbon dioxide or carbon monoxide used in the thermochemical regeneration described here can be harvested from readily available sources of $CO_2$, such as from central power plants, coking, and calcining operations that burn hydrocarbons, breweries, and bakeries. The system obtains hydrogen from biomass waste dissociation (720). The harvested $CO_2$ can be used to produce liquid feedstocks for production of chemicals and or fuels by reacting with the biomass waste produced low density hydrogen (730). For example, the methanol fuel produced in the described thermochemical regeneration of $CO_2$ with hydrogen can be used to power gasoline and diesel engines adapted to burn methanol in a non-polluting manner. U.S. Pat. Nos. 6,155,212 and 6,756,140 describe apparatus and techniques for adapting gasoline and diesel engines to burn methanol, the entire contents of which are incorporated by reference.

Equations 6 and 7 below illustrate hydrogen and carbon repurposing or recycling via methanol production in which biomass produced hydrogen is reacted with industrial process produced carbon monoxide (CO) and $CO_2$ respectively.

$$CO + 2H_2CH_3OH \ (\Delta H = -21.66 \ Kcal/g\text{-}mol) \quad \text{Equation 6}$$

$$CO_2 + 3H_2 \rightarrow CH_3OH + H_2O \ (\Delta H = -11.83 \ Kcal/g\text{-}mol) \quad \text{Equation 7}$$

The described thermochemical regeneration reactions that recycle or repurpose hydrogen, CO and $CO_2$ provide a bridge technology for increasing the financial return on past investments in equipment by utilizing existing transportation engines and storage tanks to enable thermochemical regeneration reactions to produce hydrogen-characterized fuels for achieving longer engine life and greater fuel efficiency along with greatly reduced emissions of carbon dioxide, hydrocarbons, oxides of nitrogen and particulates.

The methanol synthesis process summarized in Equations 6 and 7 may be implemented by various steps including catalytic synthesis at 95 to 100 atmospheres pressure and 500° F. (260° C.) (740). Catalysts for the processes of Equations 6 and 7 can include copper-zinc-oxide and deposited sinter mixture of copper and copper-zinc oxide at various process synthesis conditions including about 260° C. (500° F.) and 1500 psi to produce methanol or methanol and water as shown. Alternatively, dimethyl ether (DME) or ethylene or propylene may be produced depending upon the pressure, temperature and catalysts chosen.

Methanol produce by the thermochemical regeneration reactions as described above (see Equations 6 and 7) can be inexpensive, storable and transportable. In one implementation of the carbon-neutral hydrogen storage operation, methanol is synthesized from sources that ordinarily source emissions of $CO_2$. Such $CO_2$ can be captured from ethanol plants, bakeries, breweries, Portland cement plants, and fossil burning power plants and/or by atmospheric "scrubbing" to extract up to about three molecules of carbon dioxide from ten thousand molecules of air.

Similar to ethanol, methanol can be blended with gasoline up to 20% in conventional engines and 85% in flex fuel vehicles with no modifications to the vehicle or existing transportation fuel infrastructure. For years, methanol, with an octane rating of 100, has been used as a racing fuel for high-performance cars and dragsters.

Primary use of alcohols such as methanol as an energy carrier is economically and energetically favorable. For example, one liter of methanol at ambient temperature contains more hydrogen than one liter of liquid hydrogen that must be maintained in storage at −421° F.

Figure 8:
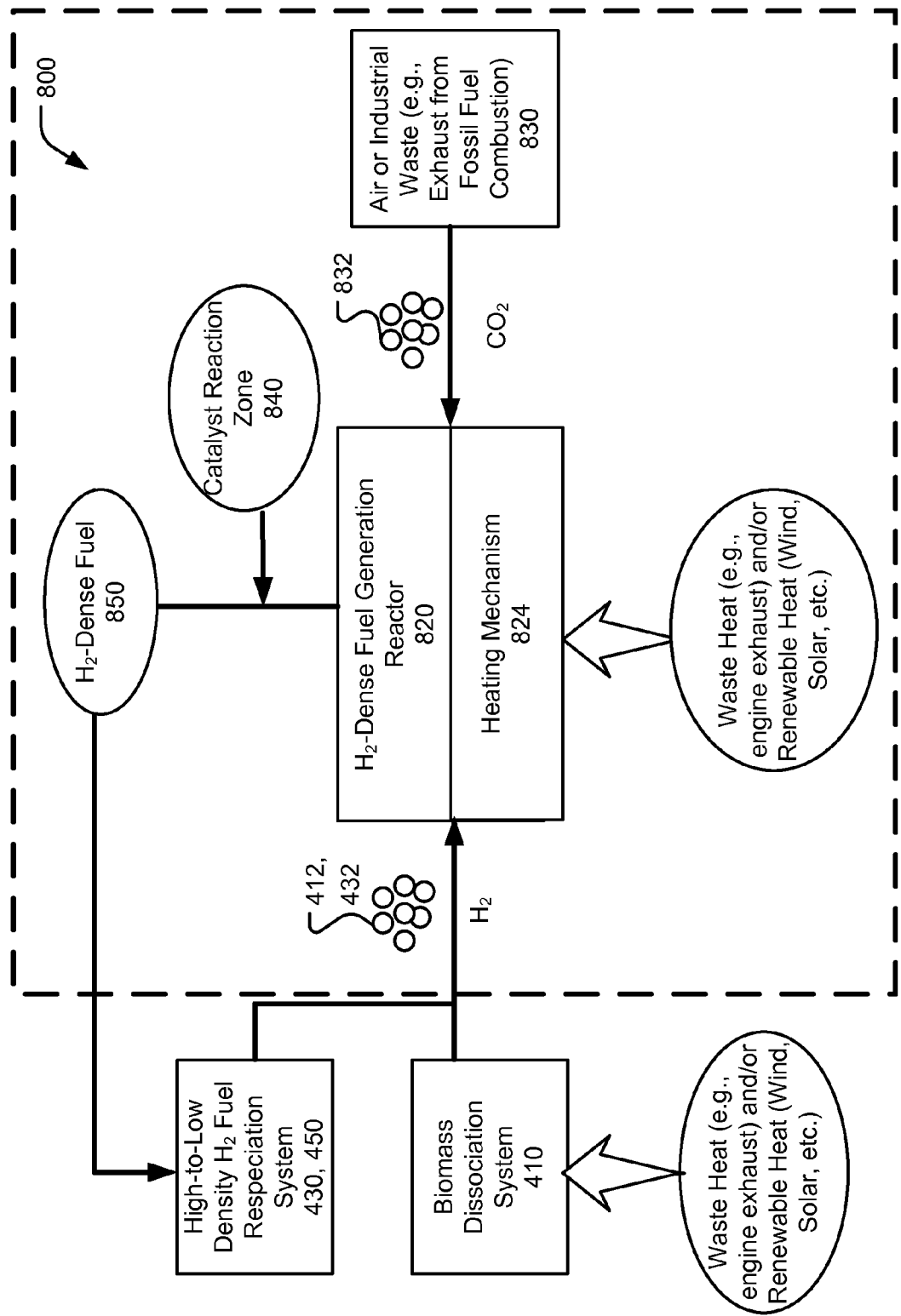
FIG. 8 is a block diagram showing an exemplary system for repurposing or recycling $CO_2$ harvested from industrial processes as waste to create renewable fuel by reacting with biomass produced hydrogen.

FIG. 8 is a block diagram showing an exemplary system 800 for repurposing or recycling $CO_2$ harvested from industrial processes as waste to create renewable fuel by reacting with biomass produced hydrogen. The system 800 receives the low density hydrogen fuel 412, 432 from the biomass dissociation system 410 or the high-to-low density hydrogen fuel respeciation system 430, 450. The heat used to dissociate the biomass waste can include waste heat from engine exhausts, engine cooling system etc. that otherwise would be released to the environment. Also, one or more of renewable energy sources, such as wind, solar, etc. can be used to generate the heat.

The received low specific energy or low density hydrogen (from dissociation of hydrocarbons, for example) is captured and forwarded to hydrogen-dense fuel generating reactor 820, which includes a heating mechanism 824. The hydrogen-dense fuel generating reactor 820 also receives carbon donors, such as $CO_2$ 832 harvested from industrial processes (e.g., exhaust gases from fossil fuel combustion or air). The hydrogen-dense fuel generating reactor 820 causes the low specific energy hydrogen to react with the harvested carbon donors, such as $CO_2$ 832 to generate hydrogen-dense fuel 850, such as methanol. The carbon donor 832 can be obtained from air or industrial waste 830, including stack smoke, waste stream of a polymer plant, etc.

The system 800 can include a catalyst reaction zone 840 to receive one or more catalysts that enhances the generation of the hydrogen-dense fuel mixture. Examples of catalysts are described above.

The generated hydrogen-dense fuel mixture 850 is storable and transportable. Because the hydrogen-dense fuel mixture 850 carry hydrogen fuel in a transportable form, the hydrogen-dense fuel mixture operates as a vehicle for carry energy to a desired destination. The hydrogen-dense fuel 850 mixture can be self-transported to a high-to-low density hydrogen fuel respeciation system (e.g., 430 or 450).

In some implementations, pressurized hydrogen or pressurized and heated hydrogen can be added to pressurize the products of reacting hydrogen and CO to form a desired compound such as DME fuel or methanol as shown in Equation 8.

$$CO+H_2+H_2 \rightarrow CH_3OH \qquad \text{Equation 8}$$

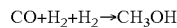

Liquid fuel such as methanol provided by the processes summarized in Equation 8 can readily be stored, transported, metered and dispensed by equipment and systems typically utilized for diesel, gasoline, and other alcohol fuels.

Repurposing or recycling of oxides of carbon such as carbon dioxide or carbon monoxide from air-burning processes generally poses the problem of separation or accommodation of nitrogen contamination. Another process variation for preparation of values from mixtures of reactive ionic species is provided by arc, corona, microwave, or radiative ionization. Mixtures of carbon monoxide and hydrogen and such nitrogen can be reacted to produce $CH_3OH$ and $NH_3$ as shown in Equation 9.

$$CO+5H_2+N_2+ENERGY \rightarrow CH_3OH+2NH_3 \qquad \text{Equation 9}$$

Ammonia ($NH_3$) produced by this or other reactions that utilize hydrogen produced by the biomass dissociation system 410 or the high-to-low density hydrogen fuel generation system 430 and 450 can be safely stored and conveyed. This provides compact storage and may serve as a precursor of hydrogen. Ammonia can be stored in various ways including as a pressurized liquid, a salt such as ammonium chloride, or in activated media such as carbon and pressurization can be accomplished by heat addition. Decomposition of ammonia as it passes a catalyst may be utilized to pressurize the $N_2$ and hydrogen products including pressurization of carbon monoxide and hydrogen that may be co-produced from methanol or wet methanol.

Figure 9:
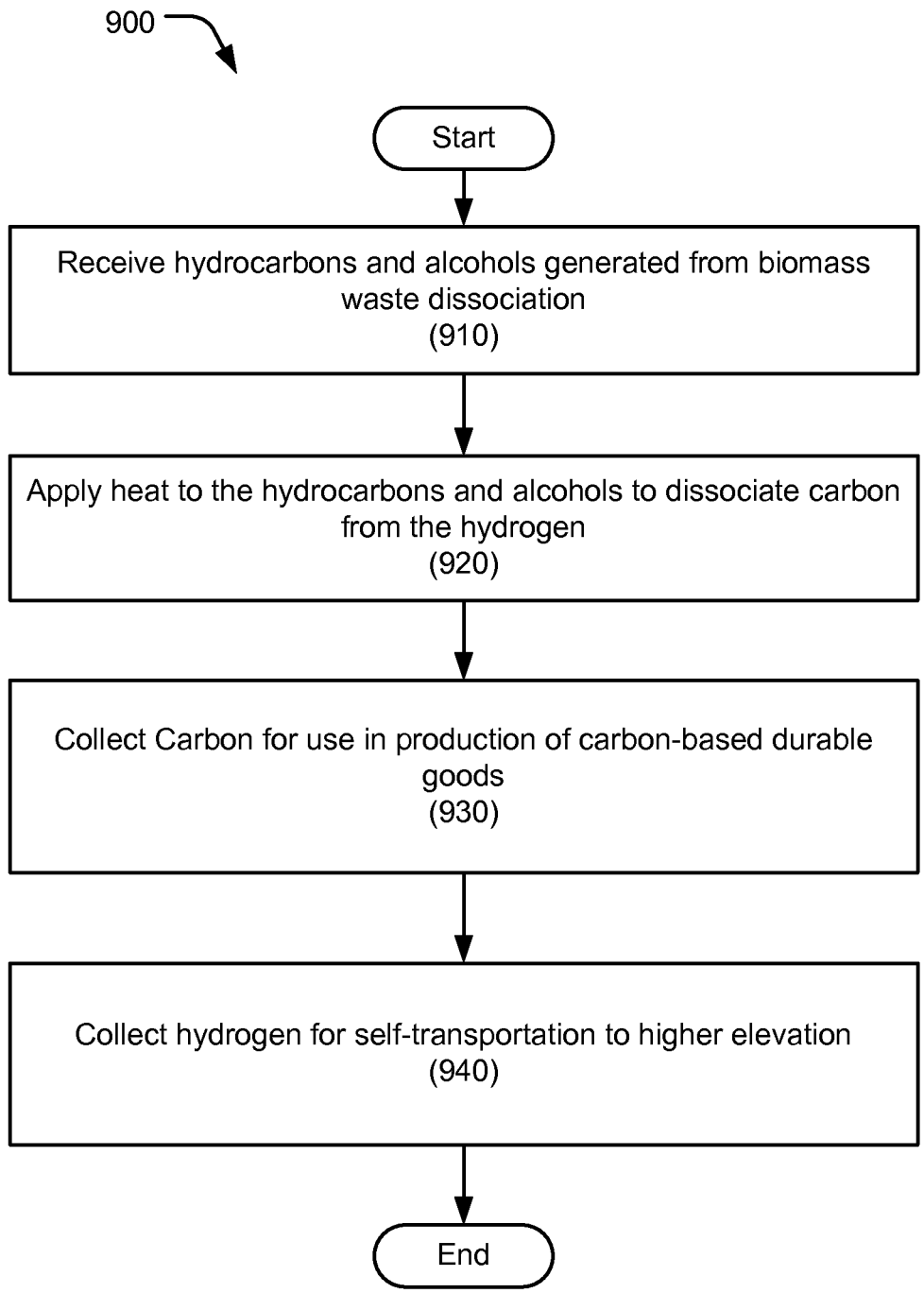
FIG. 9 is a process flow diagram of a process for dissociating hydrocarbons and alcohols to obtain carbon and hydrogen.

Respeciation of High Density hydrogen Carrier to Generate Low Density hydrogen Fuel The high density hydrogen carriers, such as hydrocarbons (e.g., methane) and alcohols (e.g., methanol) received from the low-to-high density hydrogen carrier respeciation systems 420 and 440, can be dissociated to produce low density hydrogen fuel and carbon for a multitude of "specialized carbon" applications ranging from diamond plating and semiconductors to composite structures that are stronger than steel and lighter than aluminum. FIG. 9 is a process flow diagram of a process 900 for dissociating hydrocarbons and alcohols to obtain carbon and hydrogen. A reactor (e.g., reactor 1000) can receive hydrocarbons and alcohols dissociated from biomass waste (910). The reactor can apply adequate heat and pressure to the hydrocarbons and alcohols to dissociate carbon from hydrogen (920). Equation 10 illustrates a general process of dissociating hydrocarbon fuel to obtain hydrogen and carbon. Equation 11 shows a specific reaction for dissociation of methane into carbon and hydrogen.

$$C_xH_y + HEAT_4 \rightarrow XC + 0.5Y\ H_2 \qquad \text{Equation 10}$$

$$CH_4 + \Delta H_{298K} \rightarrow 2H_2 + C\ (\Delta H_{298K} = 79.4\ kJ/mol) \qquad \text{Equation 11}$$

Equation 12 shows a reaction for dissociating cellulose and fuel alcohols that contain oxygen by anaerobic decomposition to obtain carbon, carbon monoxide and hydrogen.

$$C_2H_5OH + HEAT \rightarrow C + CO + 3H_2 \qquad \text{Equation 12}$$

The carbon monoxide can be reacted in an anaerobic dissociation shown in Equation 13 to increase the yield of hydrogen from feedstocks that contain carbon, hydrogen and oxygen:

$$CO + H_2O \rightarrow CO_2 + H_2 + HEAT \qquad \text{Equation 13}$$

Total energy value of hydrogen and carbon monoxide produced in the endothermic reactions can be 15 to 20% greater than that of methane used to source the carbon monoxide and hydrogen as shown in Equation 13. Also, to increase the thermochemical efficiency of the reactions, the heat used to dissociate the hydrocarbons can be harvested and recycled from engine exhaust (e.g., waste heat) or a renewable energy source, such as solar or wind energy.

The carbon dissociated in the processes can be collected for use in the production of carbon-based durable goods (930). For example, the carbon extracted from biomass waste-produced hydrocarbons and alcohols can be used to generate carbon products including activated carbon, fibrous carbon, diamond-like coatings, graphitic components, and carbon black. These forms of carbon products can be used to manufacture durable goods, such as better equipment to harness solar, wind, moving water, and geothermal resources along with transportation components that are stronger than steel and lighter than aluminum. Recycling or repurposing carbon to produce equipment that harnesses renewable resources provides many times more energy than burning such carbon one time. Also, the hydrogen co-produced with carbon from the dissociation of hydrocarbons and alcohols can be collected for self-transportation to a higher elevation location (940).

Figure 10:
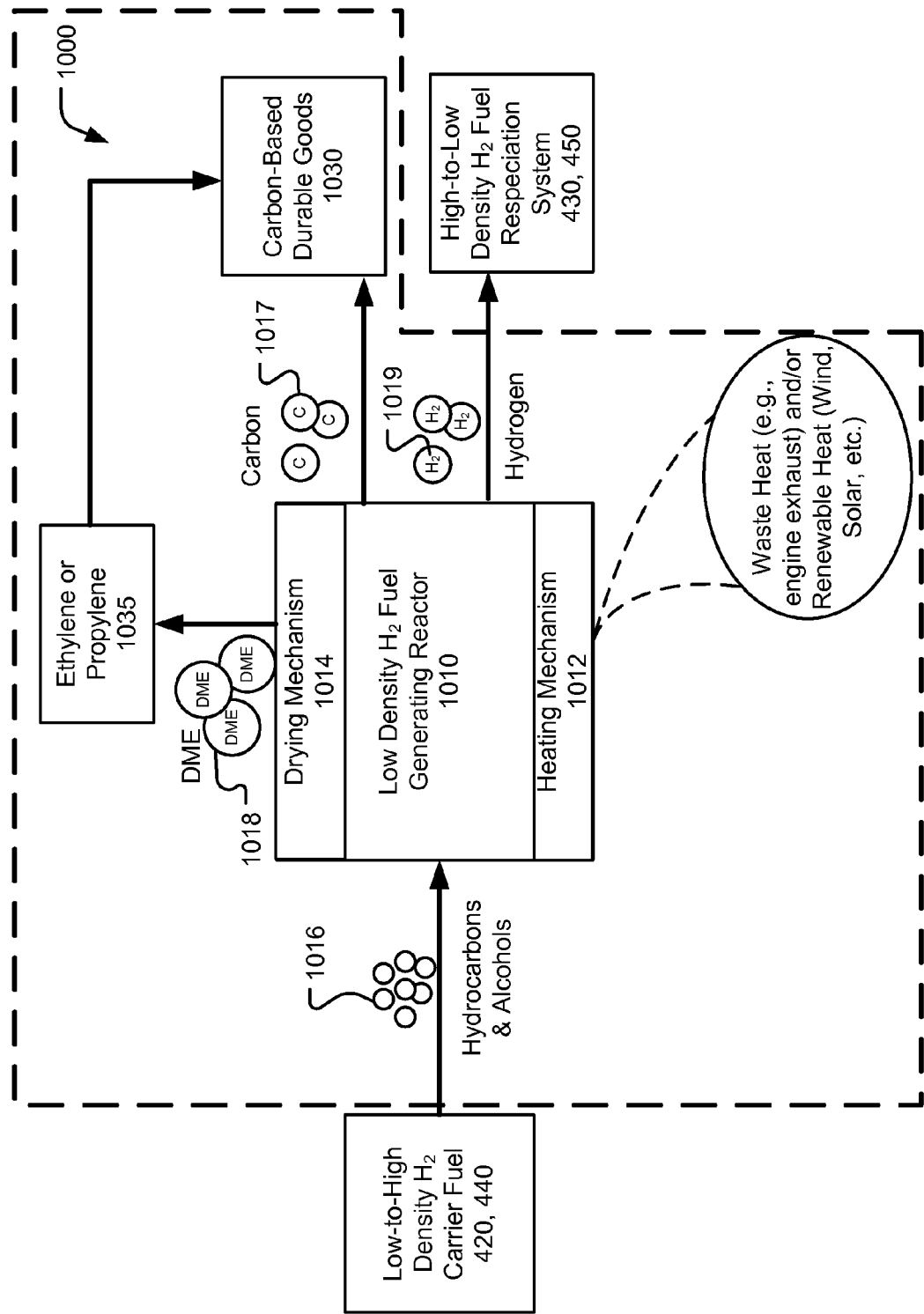
FIG. 10 is a block diagram of a system for respeciating high density hydrogen carrier fuel to generate low density hydrogen fuel.

FIG. 10 is a block diagram of a system 1000 for respeciating high density hydrogen carrier fuel to generate low density hydrogen fuel. In addition, the system 1000 can generate carbon-based durable goods from carbons co-produced with the low density hydrogen fuel. The system 1000 includes a reactor 1010 that receives the high density hydrogen carriers, such as hydrocarbons and alcohols 1016 from the low-to-high density hydrogen carrier fuel respeciation system 420, 440. The reactor 1010 can include a heating mechanism 1012, such as heat exchangers for applying the heat used in the anaerobic reactions of Equations 10-12. The low density hydrogen fuel 1019 generated from dissociation of the high density hydrogen carriers, such as hydrocarbons and alcohols 1016 can be self-transported to a higher elevation location as needed (e.g., to High-to-Low Density H$_2$Fuel Respeciation System 430, 450). Also, the carbon 1017 dissociated from the hydrocarbons and alcohols can be used in production of durable goods 1030.

The reactor 1010 can also include a drying mechanism 1014 for de-hydrating the alcohols to create DME 1018, which can be used to produce ethylene or propylene 1035. Also, the heating mechanism 1012 can be used to dehydrate the alcohols. The produced ethylene or propylene can be used to generate polymers for producing various plastics and other carbon-based durable goods 1030.

In some implementations, hydrocarbons received from a higher elevation location can be reacted with a carbon donor, such as $CO_2$ harvested from industrial processes. It can be advantageous to utilize a renewable energy resource (e.g., methane from biomass) to provide carbon for processing carbon dioxide into carbon monoxide as shown in Equation 14.

$$CH_4 + CO_2 + ENERGY \rightarrow 2CO + 2H_2 \qquad \text{Equation 14}$$

The heat used in the reaction of the harvested $CO_2$ with the biomass waste generated carbon donor can include waste heat from engine exhausts, engine cooling system etc. that otherwise would be released to the environment. Also, one or more of renewable energy sources, such as wind, solar, etc. can be used to generate the heat.

Higher pressure hydrogen can be used to pressurize the products of hydrocarbon dissociation, such as carbon monoxide and hydrogen. Also, the higher pressure hydrogen can be produced by other energy induced dissociations including electrolysis of anaerobically developed acids and liquors from organic digestion processes and from water as generally shown in Equations 15 and 16.

$$C_2H_4O_2 + 2H_2O + ENERGY \rightarrow 2CO_2 + 4H_2 \qquad \text{Equation 15}$$

$$H_2O + ENERGY \rightarrow 0.5O_2 + H_2 \qquad \text{Equation 16}$$

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

To the extent not previously incorporated herein by reference, the present application incorporates by reference in their entirety the subject matter of each of the following materials: U.S. Patent Application No. 13/027,208, filed on Feb. 14, 2011 now U.S. Pat. No. 9,206,045 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. Patent Application No. 13/026,996, filed on Feb. 14, 2011 now US Patent No 9,206,045 and titled REACTOR VESSELS WITH TRANS- MISSIVE SURFACES FOR PRODUCING HYDROGEN-BASED FUELS AND STRUCTURAL ELEMENTS, AND ASSOCIATED SYSTEMS AND METHODS; U.S. Pat. No. 13/027,015, filed on Feb. 14, 2011 and titled CHEMICAL REACTORS WITH RE-RADIATING SURFACES AND ASSOCIATED SYSTEMS AND METHODS; U.S. Patent Application No 13/027,244, filed on Feb. 14, 2011 and titled THERMAL TRANSFER DEVICE AND ASSOCIATED SYSTEMS AND METHODS; U.S. Patent Application No. 13/026,990, filed on Feb. 14, 2011, now U.S. Pat. No. 8,187,549 and titled CHEMICAL REACTORS WITH ANNULARLY POSITIONED DELIVERY AND REMOVAL DEVICES, AND ASSOCIATED SYSTEMS AND METHODS; U.S. Patent Application No 13/027,181, filed on Feb. 14, 2011, now U.S. Pat. No. 8,187,550 and titled REACTORS FOR CONDUCTING THERMO-CHEMICAL PROCESSES WITH SOLAR HEAT INPUT, AND ASSOCIATED SYSTEMS AND METHODS; U.S. Patent Application No. 13/027,215, filed on Feb. 14, 2011 and titled INDUCTION FOR THERMOCHEMICAL PROCESS, AND ASSOCIATED SYSTEMS AND METHODS; U.S. Patent Application No. 13/027,198, filed on Feb. 14, 2011, now U.S. Pat. No. 9,188,086, and titled COUPLED THERMOCHEMICAL REACTORS AND ENGINES, AND ASSOCIATED SYSTEMS AND METHODS; U.S. Patent application No. 61/385,508, filed on Sep. 22, 2010 and titled REDUCING AND HARVESTING DRAG ENERGY ON MOBILE ENGINES USING THERMAL CHEMICAL REGENERATION; U.S. Patent Application No. 13/027,060, filed on Feb. 14, 2011, now U.S. Pat. No. 8,318,100, and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. Patent application No. 61/237,419, filed on Aug. 27, 2009 and titled CARBON SEQUESTRATION; U.S. Patent Application No. 13/027,068, filed on Feb. 14, 2011, now U.S. Patent No 8,318,997 and titled CARBON-BASED DURABLE GOODS AND RENEWABLE FUEL FROM BIOMASS WASTE DISSOCIATION; U.S. Patent Application No. 13/027,196, filed on Feb. 14, 2011, now U.S. Pat. No, 8,912,239, and titled CARBON RECYCLING AND REINVESTMENT USING THERMOCHEMICAL REGENERATION; U.S. Patent Application No. 13/027,195, filed on Feb. 14, 2011, and titled OXYGENATED FUEL; U.S. Patent application No. 61/237,425, filed on Aug. 27, 2009 and titled OXYGENATED FUEL PRODUCTION; and U.S. Patent Application No. 13/027, 197, filed on Feb. 14, 2011, now U.S. Pat. No. 8,070,835 and titled MULTI-PURPOSE RENEWABLE FUEL FOR ISOLATING CONTAMINANTS AND STORING ENERGY.

I claim:

1. A method of transporting renewable fuel, the method comprising:
generating low density hydrogen fuel from biomass dissociation at a first location of a low elevation;
self-transporting the low density hydrogen fuel in a pipeline to a second location at a higher elevation than the first location, wherein the low density hydrogen fuel travels from the first location to the second location without adding energy or pressure;
generating a high density hydrogen carrier at the second location of higher elevation by reacting the low density hydrogen fuel with at least one of a carbon donor, a nitrogen donor and an oxygen donor; and
delivering the high density hydrogen carrier to a third location of a lower elevation than the second location while providing pressure or kinetic energy.

2. The method of claim 1, wherein generating the low density hydrogen fuel comprises applying waste heat recovered from an external energy source or heat generated from a renewable energy source.

3. The method of claim 1, wherein the high density hydrogen carrier comprises at least one of hydrocarbon, alcohol and ammonia.

4. The method of claim 3, wherein the hydrocarbon comprises at least one of methane and ethane; and
wherein the alcohol comprises at least one of methanol and ethanol.

5. The method of claim 1, wherein the carbon donor comprises carbon dioxide and the hydrogen donor comprises water.

6. The method of claim 1, further comprising:
dissolving a hazardous contaminant in the high density hydrogen carrier to generate a liquid mixture that isolates the hazardous contaminant from an environment.

7. The method of claim 6, wherein the liquid mixture controls a vapor pressure or availability of the vapor pressure.

8. The method of claim 6, further comprising:
applying heat to the liquid mixture to generate oxygenated fuel mixture with a ratio of hydrogen to carbon that is higher than the high density hydrogen carrier.

9. The method of claim 8, further comprising:
transporting in a pipeline the hydrogen generated from the liquid mixture to a fourth location at a higher elevation than the third location without adding energy or pressure.

10. The method of claim 1, further comprising:
applying heat to the high density hydrogen carrier to generate oxygenated fuel with a ratio of hydrogen to carbon that is higher than the high density hydrogen carrier.

11. The method of claim 1, further comprising:
transporting in a pipeline the hydrogen generated from the high density hydrogen carrier to a fourth location at a higher elevation than the third location without adding energy or pressure.

12. The method of claim 1, wherein the at least one of a carbon donor, a nitrogen donor and an oxygen donor are harvested from industrial waste.

13. A pipeline system of transporting renewable fuel, the system comprising:
a biomass conversion plant at a first location of a low elevation to generate low density hydrogen fuel from biomass dissociation;
a first pipeline connecting the biomass conversion plant to a second location of a higher elevation than the first location, wherein the low density hydrogen fuel travels within the pipeline from the first location to the second location without added energy of pressure;
a thermochemical reactor connected to the second location of the higher elevation to generate a high density hydrogen carrier, wherein the thermochemical reactor reacts the low density hydrogen fuel with at least one of a carbon donor, a nitrogen donor and an oxygen donor; and
a second pipeline connecting the thermochemical reactor to a third location of a lower elevation than the second location, wherein the high density hydrogen carrier is delivered to the third location with at least one of pressure or kinetic energy generated by the high density hydrogen carrier.

14. The pipeline system of claim 13, wherein the thermochemical reactor comprises a countercurrent heat exchanger to apply waste heat recovered from an external energy source or heat generated from a renewable energy source.

15. The pipeline system of claim 13, wherein the high density hydrogen carrier comprises at least one of hydrocarbon, alcohol and ammonia.

16. The pipeline system of claim 15, wherein the hydrocarbon comprises at least one of methane and ethane; and
wherein the alcohol comprises at least one of methanol and ethanol.

17. The pipeline system of claim 13, wherein the carbon donor comprises carbon dioxide and the hydrogen donor comprises water.

18. The pipeline system of claim 13, further comprising:
a contaminant recovery system connected to the thermochemical reactor, the contaminant recovery system configured to
harvest a hazardous contaminant; and
dissolve the harvested hazardous contaminant in the high density hydrogen carrier to generate a liquid mixture that isolates the hazardous contaminant from an environment.

19. The pipeline system of claim 18, wherein the liquid mixture controls a vapor pressure or availability of the vapor pressure.

20. The pipeline system of claim 18, wherein the liquid mixture is transported in the second pipeline to the third location using at least one of pressure and kinetic energy generated by the liquid mixture.

* * * * *